(12) United States Patent
Fife et al.

(10) Patent No.: US 11,426,143 B2
(45) Date of Patent: Aug. 30, 2022

(54) VERTICAL PACKAGING FOR ULTRASOUND-ON-A-CHIP AND RELATED METHODS

(71) Applicant: BFLY Operations, Inc., Guilford, CT (US)

(72) Inventors: Keith G. Fife, Palo Alto, CA (US); Jianwei Liu, Fremont, CA (US)

(73) Assignee: BFLY OPERATIONS, INC., Guilford, CT (US)

( * ) Notice: Subject to any disclaimer, the term of this patent is extended or adjusted under 35 U.S.C. 154(b) by 0 days.

(21) Appl. No.: 17/088,336

(22) Filed: Nov. 3, 2020

(65) Prior Publication Data

US 2021/0113188 A1     Apr. 22, 2021

Related U.S. Application Data

(63) Continuation of application No. 16/401,249, filed on May 2, 2019, now Pat. No. 10,856,844.
(Continued)

(51) Int. Cl.
*H01L 29/84*     (2006.01)
*A61B 8/00*     (2006.01)
(Continued)

(52) U.S. Cl.
CPC .......... *A61B 8/4477* (2013.01); *A61B 8/4483* (2013.01); *H01L 41/1132* (2013.01); *H01L 41/293* (2013.01)

(58) Field of Classification Search
None
See application file for complete search history.

(56) References Cited

U.S. PATENT DOCUMENTS

| | | | |
|---|---|---|---|
| 5,493,541 A * | 2/1996 | Snyder | H04R 17/00 310/365 |
| 7,741,686 B2 * | 6/2010 | Khuri-Yakub | H01L 27/1203 257/416 |

(Continued)

OTHER PUBLICATIONS

International Search Report and Written opinion dated Jul. 24, 2019 in connection with International Application No. PCT/US2019/030480.
(Continued)

*Primary Examiner* — Hung K Vu
(74) *Attorney, Agent, or Firm* — Osha Bergman Watanabe & Burton LLP

(57) ABSTRACT

Vertical packaging configurations for ultrasound chips are described. Vertical packaging may involve use of integrated interconnects other than wires for wire bonding. Examples of such integrated interconnects include edge-contact vias, through silicon vias and conductive pillars. Edge-contact vias are vias defined in a trench formed in the ultrasound chip. Multiple vias may be provided for each trench, thus increasing the density of vias. Such vias enable electric access to the ultrasound transducers. Through silicon vias are formed through the silicon handle and provide access from the bottom surface of the ultrasound chip. Conductive pillars, including copper pillars, are disposed around the perimeter of an ultrasound chip and provide access to the ultrasound transducers from the top surface of the chip. Use of these types of packaging techniques can enable a substantial reduction in the dimensions of an ultrasound device.

20 Claims, 12 Drawing Sheets

Related U.S. Application Data

(60) Provisional application No. 62/666,560, filed on May 3, 2018.

(51) Int. Cl.
  *H01L 41/293* (2013.01)
  *H01L 41/113* (2006.01)

(56) References Cited

U.S. PATENT DOCUMENTS

| | | | |
|---|---|---|---|
| 7,825,509 B1 * | 11/2010 | Baumhauer, Jr. | H01L 24/49 |
| | | | 257/724 |
| 7,846,102 B2 | 12/2010 | Kupnik | |
| 8,076,739 B2 * | 12/2011 | Schmollngruber | B81B 7/0006 |
| | | | 257/419 |
| 8,193,685 B2 | 6/2012 | Klee et al. | |
| 8,207,652 B2 * | 6/2012 | Baumgartner | A61B 8/4483 |
| | | | 310/334 |
| 2009/0148967 A1 | 6/2009 | Wodnicki et al. | |
| 2011/0055447 A1 | 3/2011 | Costa | |
| 2014/0293751 A1 * | 10/2014 | Dekker | B06B 1/0292 |
| | | | 367/181 |
| 2019/0336103 A1 | 11/2019 | Fife et al. | |

OTHER PUBLICATIONS

International Preliminary Report on Patentability dated Nov. 12, 2020 in connection with International Application No. PCT/US2019/030480.

* cited by examiner

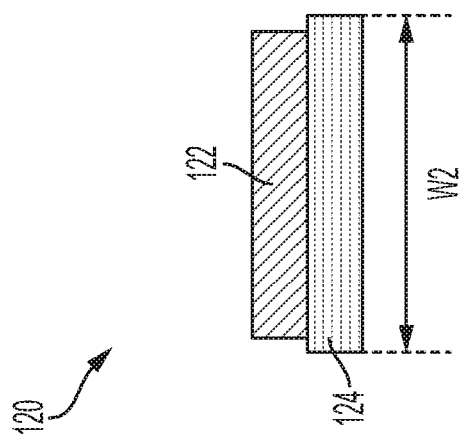
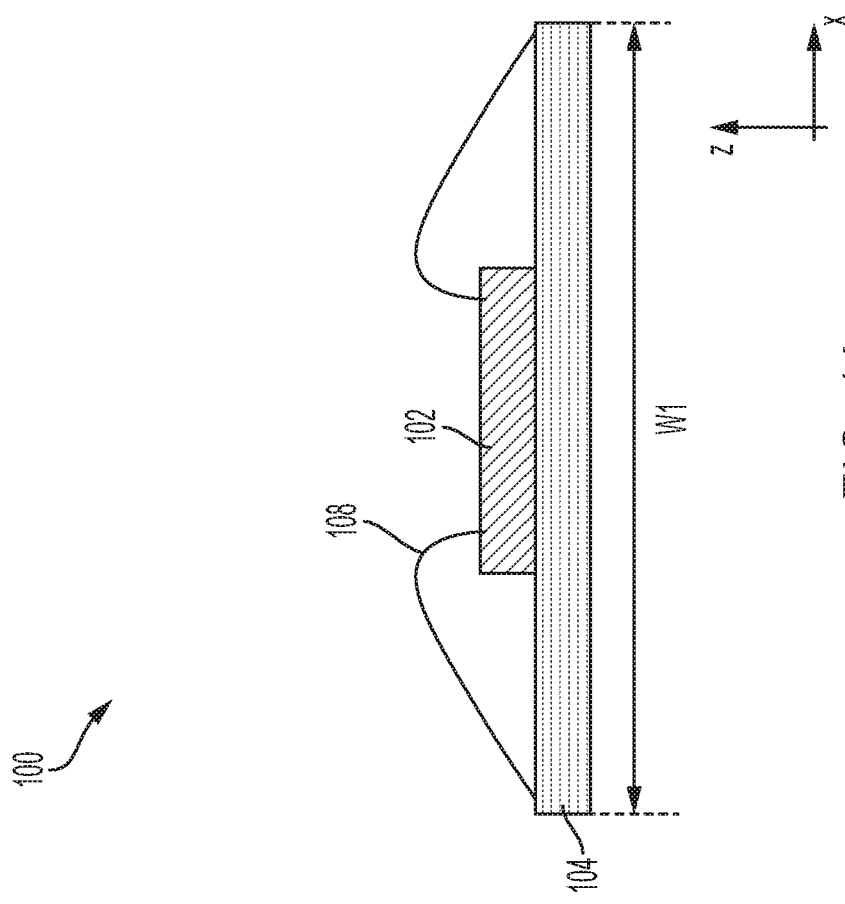

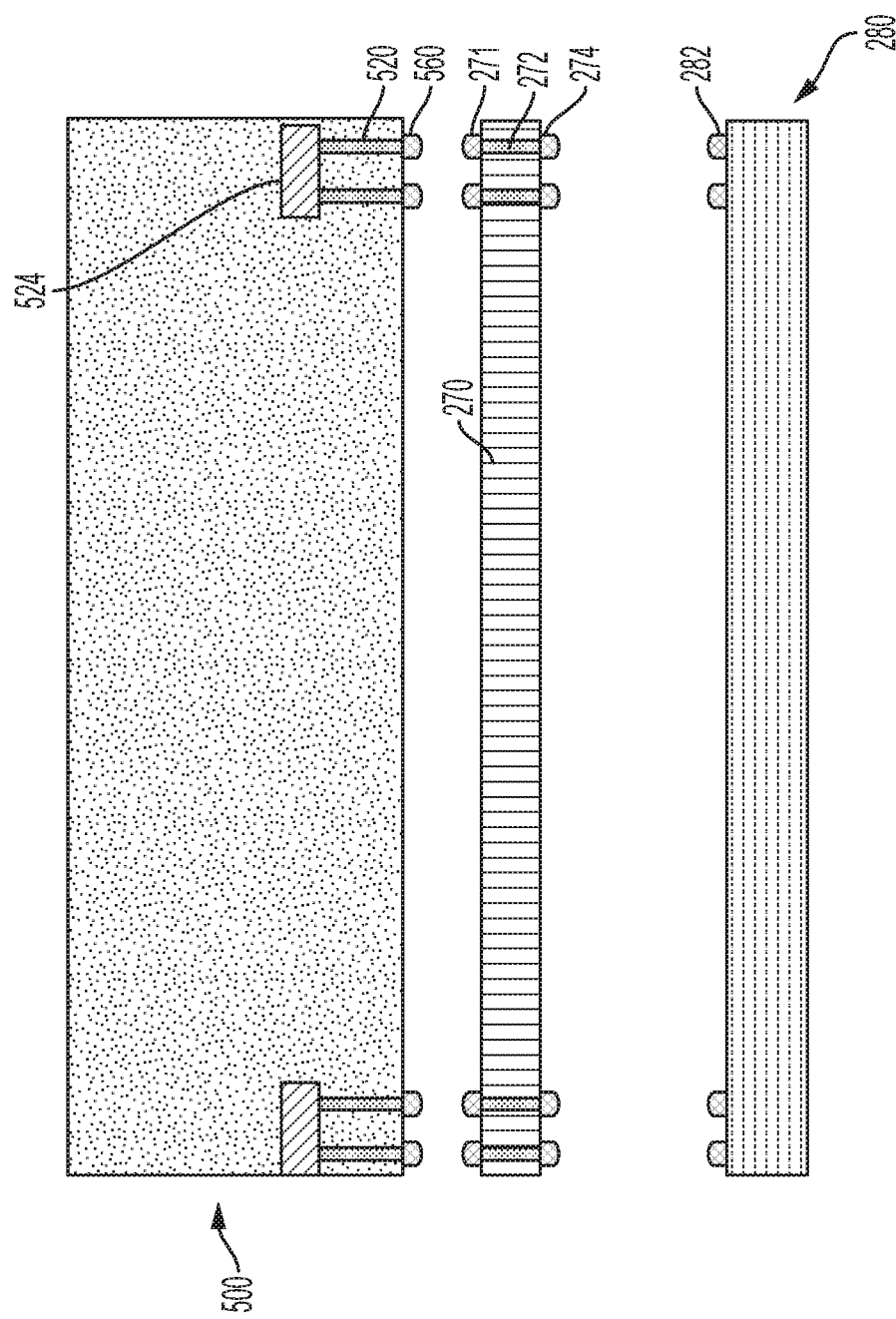

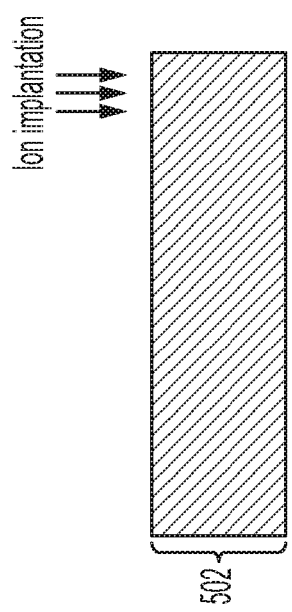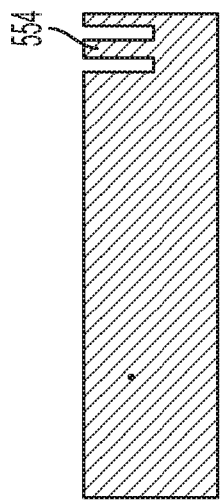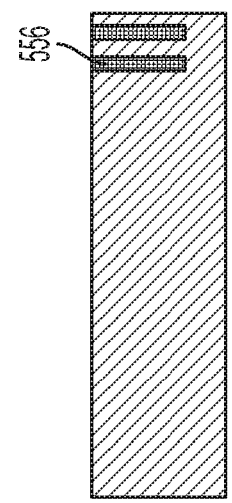

VERTICAL PACKAGING FOR ULTRASOUND-ON-A-CHIP AND RELATED METHODS

CROSS-REFERENCE TO RELATED APPLICATION

This application is a continuation claiming the benefit under 35 U.S.C. § 120 of U.S. application Ser. No. 16/401,249, filed May 2, 2019, and entitled "VERTICAL PACKAGING FOR ULTRASOUND-ON-A-CHIP AND RELATED METHODS," which is hereby incorporated herein by reference in its entirety.

U.S. application Ser. No. 16/401,249 claims the benefit under 35 U.S.C. § 119(e) of U.S. Provisional Patent Application Ser. No. 62/666,560, filed May 3, 2018, and entitled "VERTICAL PACKAGING FOR TRANSDUCER ON CMOS SENSOR," which is hereby incorporated herein by reference in its entirety.

BACKGROUND

Field

The present application relates to micromachined ultrasound transducers.

Related Art

Some micromachined ultrasound transducers include a flexible membrane suspended above a substrate. A cavity is located between part of the substrate and the membrane, such that the combination of the substrate, cavity, and membrane form a variable capacitor. If actuated, the membrane may generate an ultrasound signal. In response to receiving an ultrasound signal, the membrane may vibrate, resulting in an output electrical signal.

BRIEF SUMMARY

Some embodiments relate to an ultrasound device comprising an ultrasound-on-a-chip having a first surface configured to be mounted to a substrate, the ultrasound-on-a-chip comprising an array of ultrasound transducers; and an integrated interconnect for electrically connecting the substrate to at least one ultrasound transducer of the array of ultrasound transducers, at least a portion of the integrated interconnect extending in a direction angled with respect to the first surface.

In some embodiments, the ultrasound-on-a-chip comprises a trench and the integrated interconnect comprises one or more vias formed in the trench.

In some embodiments, at least a portion of the trench is lined with an insulative material.

In some embodiments, the integrated interconnect further comprises a conductive layer disposed over the insulative material.

In some embodiments, the ultrasound device further comprises a bond pad formed on the first surface of the ultrasound-on-a-chip and in electrical communication with at least one via of the one or more vias.

In some embodiments, the trench is formed through the first surface.

In some embodiments, the at least one ultrasound transducer of the array of ultrasound transducers comprises an electrode proximate the first surface and in electrical connection with a first via of the one or more vias; a membrane proximate a second surface of the ultrasound-on-a-chip opposite the first surface, the membrane being in electrical connection with a second via of the one or more vias; and a cavity formed between the electrode and the membrane.

In some embodiments, the integrated interconnect comprises a conductive pillar and a conductive layer electrically connecting the conductive pillar to the at least one ultrasound transducer.

In some embodiments, the ultrasound-on-a-chip comprises a second surface opposite the first surface, the conductive layer being adjacent the second surface.

In some embodiments, the conductive pillar extends in a direction substantially perpendicular to the first surface and the conductive layer extends in a direction substantially parallel to the first surface.

In some embodiments, the conductive pillar is embedded in a support comprising an insulative material.

In some embodiments, the integrated interconnect comprises a through-silicon-via (TSV) adjacent the first surface of the ultrasound-on-a-chip.

Some embodiments relate to an ultrasound device comprising a package having a width along a first direction that is less than 30 mm. The package comprises an ultrasound-on-a-chip comprising an array of ultrasound transducers; and an interposer spaced from the ultrasound-on-a-chip in a second direction perpendicular to the first direction.

In some embodiments, the ultrasound-on-a-chip comprises a trench and one or more vias formed in the trench, the one or more vias electrically coupling the interposer with the array of ultrasound transducers.

In some embodiments, the package further comprises:
a conductive pillar attached to the interposer and a conductive trace electrically connecting the conductive pillar to at least one ultrasound transducer of the array of ultrasound transducers.

In some embodiments, the ultrasound-on-a-chip comprises a through-silicon-via (TSV) electrically coupled to the interposer.

Some embodiments relate to an ultrasound device comprising a substrate; an ultrasound-on-a-chip disposed on the substrate and comprising an array of ultrasound transducers; and means for electrically connecting the array of ultrasound transducers to the substrate.

In some embodiments, the means comprises one or more vias integrated in the ultrasound-on-a-chip.

In some embodiments, the ultrasound-on-a-chip comprises a trench and the one or more vias are formed in the trench.

In some embodiments, the means comprises a conductive pillar attached to the substrate and a conductive trace electrically connecting the conductive pillar to at least one ultrasound transducer of the array of ultrasound transducers.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 1A is a schematic diagram of an ultrasound device including wires, according to some embodiments of the present application.

FIG. 1B is a schematic diagram of an ultrasound device including vertical integrated interconnects, according to some non-limiting embodiments of the present application.

FIG. 6 is a cross sectional view of an ultrasound chip including through silicon vias during packaging, according to some non-limiting embodiments of the present application.

FIGS. 7A-7F illustrate a fabrication sequence for forming the ultrasound chip of FIG. 5, according to some non-limiting embodiments of the present application.

DETAILED DESCRIPTION

Figure 2A:
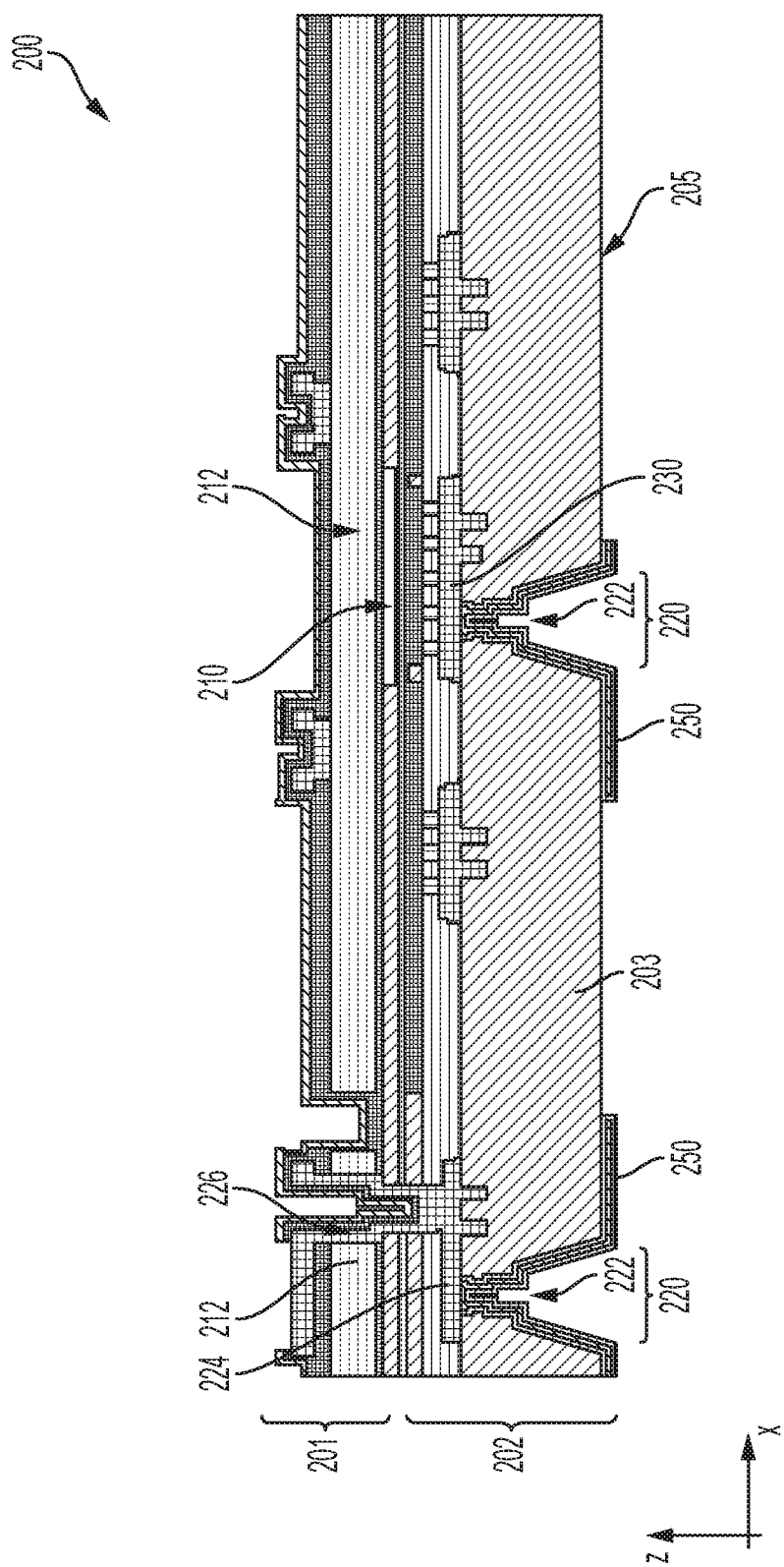
FIG. 2A is a cross-sectional view of an ultrasound chip including an edge-contact via, according to some non-limiting embodiments of the present application.

Conventional ultrasound systems are large, complex and expensive, and are typically only purchased by large medical facilities with significant financial resources. Recently, less expensive, portable, and less complex ultrasound imaging devices have been introduced. Such imaging devices include ultrasonic transducers monolithically integrated onto a single semiconductor ultrasound-on-a-chip to form a monolithic ultrasound device. Being monolithic, these devices are substantially more compact than conventional ultrasound systems.

Applicant has appreciated, however, that an additional reduction in the size of these monolithic ultrasound devices may be beneficial. Certain diagnoses that rely on ultrasound imaging require the ability to probe small anatomical features, such as the interstices that separate adjacent ribs of a patient. Small probe heads are needed to probe such small features. Applicant has appreciated that some probe heads that implement ultrasounds-on-a-chip are still too large to enable probing of such small anatomical features. Applicant has further appreciated that the relatively large size of these probe heads results from the use of wire bonding with the chip package. The relatively large size of these ultrasound chips stems from the fact that wire bonding involves the use of electrical connections that are not integrated as part of the chip. More specifically, wire bonding involves the use of discrete wires that place individual ultrasound transducers in electrical communication with the respective control circuits. Dedicated machines designed to attach the ends of a wire to the desired locations are used to perform wire bonding. Collectively, these wires can occupy more volume inside the package than the chip itself, thus posing a limit to the minimum dimension of the package.

Applicant has further appreciated that ultrasound chips including bond wires are power hungry, which may render these devices unsuitable for use in low-power applications and/or may require complex cooling devices. The relatively large power consumption results from the length of these wires, which, in turn, gives rise to large inductance. Such wires, in fact, can be as long as 3 mm or more in some implementations.

Aspects of the present application are directed to ultrasound devices that use interconnects for placing the ultrasound transducers in electrical communication with the control circuits that are integrated with the ultrasound chips. Unlike wires used for wire bonding, the integrated interconnects described herein can be made using microfabrication techniques, and consequently, are embedded in the ultrasound chip. Such interconnects may be substantially shorter than bond wires. For example, such interconnects may be shorter than 1.5 mm, shorter than 1 mm, shorter than 0.5 mm, or shorter than 0.2 mm, among other possible values.

Compared to wire bonding implementations, use of integrated interconnects can result in a substantial reduction in the overall size of the package. This, it turn, can result in a more compact probe head. Furthermore, use of integrated interconnects can result in a substantial reduction in inductance, and as a result, in power consumption. Thus, the ultrasound devices described herein can be employed in applications requiring small probe heads and/or in applications requiring low power consumption. Additionally, or alternatively, these ultrasound devices may reduce the complexity of the cooling system.

FIG. 1A illustrates a package including a wire bonded ultrasound-on-a-chip and FIG. 1B illustrates a package including an ultrasound-on-a-chip implementing integrated interconnects of the types described herein. Referring first to FIG. 1A, package 100 is designed to be mounted on a printed circuit board (not shown in FIG. 1A), and the resulting assembly to be installed in an ultrasound probe head. Package 100 includes un ultrasound-on-a-chip 102, an interposer 104 and wires 108. Ultrasound-on-a-chip 102 includes ultrasound transducers for emitting ultrasound waves and/or detecting ultrasound waves. Interposer 104 includes conductive traces for routing electrical signals between ultrasound-on-a-chip 102 and the printed circuit board.

Ultrasound-on-a-chip 102 is placed in electric communication with the conductive traces of interposer 104 by wires 108, which are deployed using wire bonding techniques. Because of the lateral extension of wires 108, which can be as long as 3 mm or more in some implementations, the lateral extension of the overall package can be large, which may limit the usefulness of the ultrasound probe head in which package 100 is disposed. In some implementations, the width of the package may impact the overall size of the ultrasound probe head, and as a result, the ability to probe small anatomical features. As a result, these ultrasound probe heads may be unsuitable for certain types of diagnoses. The width w1 of the package may be greater than 5 mm, greater than 7.5 mm, or greater than 1 cm.

Wire bonding packaging may be cumbersome in some implementations, as it may require several steps for attaching the wires to the chip. Furthermore, wire bonded packages may exhibit mechanical stress.

FIG. 1B is a schematic diagram of a package including an ultrasound-on-a-chip in which vertical packaging techniques are used instead of wire bonding, in accordance with some embodiments. Package 120 includes ultrasound-on-a-chip 122 and interposer 124. Ultrasound-on-a-chip 122 is placed in electric communication with interposer 124 by vertical integrated interconnects, examples of which include edge-contact vias, conductive pillars and through silicon vias, as described in detail further below. As shown in this figure, the absence of wires enables a substantial reduction in the width (w2) of the package. For example, in some embodiments, width w2 may be between 1 mm and 50 mm, between 1 mm and 40 mm, between 1 mm and 35 mm, between 1 mm and 30 mm, between 1 mm and 25 mm, between 1 mm and 20 mm, between 1 mm and 15 mm, between 1 mm and 10 mm or between 1 mm and 5 mm, or any other suitable range within such ranges. Other ranges are also possible.

In some embodiments, the relatively small size of package 120 may enable probing of small anatomical features. Alternatively, or additionally, the relatively small size of package 120 may enable integration of additional acoustic structures (e.g., acoustic lenses) inside the ultrasound probe head.

In some of the embodiments in which bonded wires are absent in package 120, packaging of ultrasound-on-a-chip 122 may be substantially less cumbersome than packing of ultrasound-on-a-chip 102. This is because the steps required for attaching the wires may be omitted. Furthermore, the absence of bonded wires may lead to the mechanical stress on ultrasound-on-a-chip 122 may being substantially less than the mechanical stress on ultrasound-on-a-chip 102.

Some embodiments are directed to means for electrically connecting an array of ultrasound transducers of an ultrasound-on-a-chip to a substrate (e.g., an interposer, a printed circuit board or any other type of carrier) on which the ultrasound-on-a-chip is disposed. Such means may comprise one or more edge-contact vias and/or one or more through silicon vias and/or one or more conductive pillars and/or one or more solder bumps or balls and/or a ball grid array (BGA). In some embodiments, an ultrasound-on-a-chip may be bonded to a substrate via flip-chip bonding.

The aspects and embodiments described above, as well as additional aspects and embodiments, are described further below. These aspects and/or embodiments may be used individually, all together, or in any combination of two or more, as the application is not limited in this respect.

I. EDGE-CONTACT VIAS

Some embodiments relate to vertical integrated interconnects including edge-contact vias. Edge-contact vias may provide access to ultrasound transducers through the bottom surface of an ultrasound-on-a-chip (the interface surface between an ultrasound-on-a-chip and the substrate on which the ultrasound-on-a-chip is disposed). Formation of edge-contact vias of the types described herein may involve formation of a trench through the interface surface of an ultrasound-on-a-chip and formation of one or more vias in the trench.

FIG. 2A is a cross-sectional view of an ultrasound chip comprising edge-contact vias, according to some non-limiting embodiments. Ultrasound chip 200 includes an ultrasound transducer substrate 201 and a circuit substrate 202. These substrates may be bonded to one another in any suitable way. Ultrasound transducer substrate 201 includes a plurality of ultrasound transducers and circuit substrate 202 includes circuits, such as complementary metal-oxide-semiconductor (CMOS) circuits, for controlling the operations of the ultrasound transducers. In some embodiments, ultrasound transducer substrate 201 includes capacitive micromachined ultrasound transducers (CMUTs), though other types of transducers may be used including piezoelectric MUTs (PMUTs).

The ultrasound transducers include a sealed cavity 210 formed between a membrane 212 and a bottom electrode 230. The combination of sealed cavity 210, membrane 212 and bottom electrode 230 may form a CMUT. The cavities 210 may be formed by bonding ultrasound transducer substrate 201 and circuit substrate 202 together. Membrane 212 may serve as the top electrode. In some embodiments, one or more of membrane 212 and bottom electrode 230 may include silicon. In some such embodiments, to facilitate operation as of the CMUT, membrane 212 and bottom electrode 230 may be doped to act as conductors, and in some cases may be highly doped (e.g., having a doping concentration greater than $10^{15}$ dopants/cm$^3$ or greater). When a time-varying voltage is applied between membrane 212 and bottom electrode 230, the membrane vibrates thus producing acoustic (e.g., ultrasound) waves. Additionally, when an acoustic wave hits an ultrasound transducer, a voltage arises between membrane 212 and bottom electrode 230. Accordingly, the combination of cavity 210, membrane 212 and bottom electrode 230 forms an ultrasound transducer.

Ultrasound chip 200 is designed to provide electric access from outside the chip to the bottom electrodes 230 and membranes 212 using edge-contact vias 222. The cross-sectional view of FIG. 2A illustrates two edge-contact vias, though any other suitable number of vias may be present. Each edge-contact via 222 is formed inside a trench 220, which in turn is formed in the handle (203) of circuit substrate 202. The first edge-contact via 222 of FIG. 2A (positioned on the left-hand side of ultrasound chip 200) provides electric access to a membrane 212. More specifically, this edge-contact via 222 electrically couples a bond pad 250 (formed at interface surface 205) with a pad 224. Pad 224 is coupled to a membrane 212 via conductive structure 226, which include one or more conductive portions extending parallel to the z-axis. Bond pad 250 may be placed in electrical contact with a corresponding pad formed on an underlying substrate on which ultrasound chip 200 is mounted. For example, conductive pads 250 may connected to a BGA, solder bumps, solder balls, or other surface mounting interconnects.

The second edge-contact via 222 of FIG. 2A (positioned on the right-hand side of ultrasound chip 200) provides electric access to bottom electrode 230. More specifically, this edge-contact via 222 electrically couples a bond pad 250 with a bottom electrode 230.

Figure 2B:
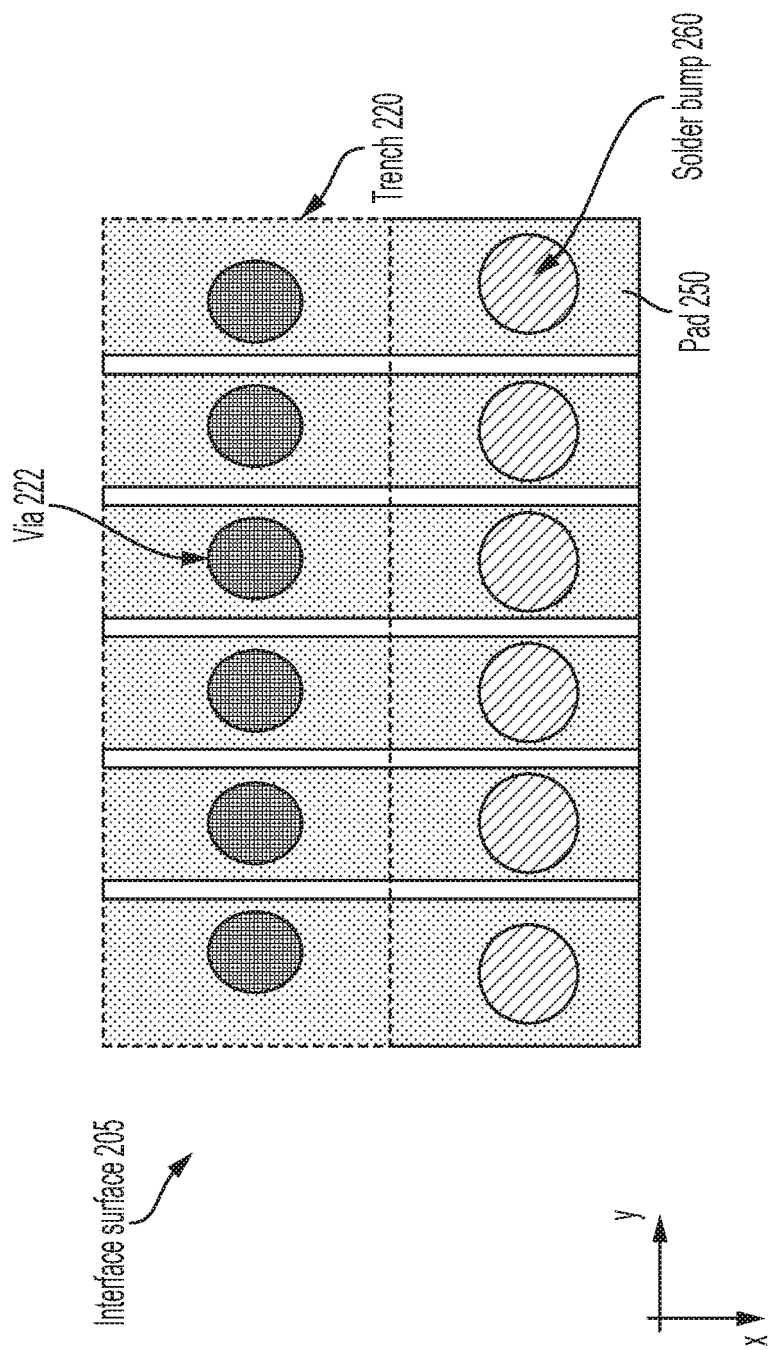
FIG. 2B is bottom view of the ultrasound chip of FIG. 2A, according to some non-limiting embodiments of the present application.

As shown in FIG. 2A, edge-contact vias 222 extend primarily in a direction that is angled with respect to interface surface 205. In this example, edge-contact via 222 extends in the vertical direction (parallel to the z-axis). Each edge-contact via 222 may be smaller (in the lateral direction and/or the vertical direction) of the trench 220 in which the via is formed. In some embodiments, a trench 220 may include more than one edge-contact via, as illustrated in FIG. 2B, a bottom view of ultrasound chip 200 at interface surface 205. This trench 220 includes six edge-contact vias 222 (though other trenches may include any other suitable number of vias). The edge-contact vias 222 may be spaced from one another in a direction parallel to the y-axis in some embodiments, or may be arranged in any other configuration. Each edge-contact via couples a bond pad 250 with a corresponding membrane 212, or a bond pad 250 with a corresponding bottom electrode 230. In this example, each bond pad 250 is connected to a solder bump 260 for enabling electrical contact with an underlying substrate.

FIGS. 3A-3F illustrate a fabrication sequence for fabricating an edge-contact via, in accordance with some non-limiting embodiments. At the process step of FIG. 3A, a trench 220 is formed through the handle 203 and, subsequently, an opening 221 is formed inside trench 220. The opening 221 may uncover the bottom surface of a pad 224

(or the bottom surface of a bottom electrode 230). Trench 220 and opening 221 may be formed using any suitable type of etching technique, including for example reactive ion etching (RIE). In some embodiments, more than one via may be formed for each trench. The depth (along the z-axis) of a trench 220 may be, among other possible values, between 50 µm and 500 µm, between 50 µm and 300 µm, between 50 µm and 200 µm, or between 50 µm and 150 µm. The width (along the x-axis or the y-axis) of a trench 220 may be, among other possible values, between 100 µm, and 500 µm, between 100 µm and 300 µm, between 200 µm and 400 µm or between 250 µm and 350 µm.

Figure 3A:
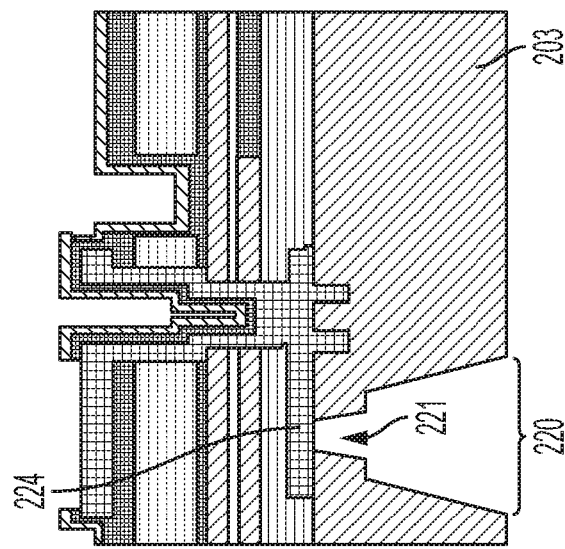
FIGS. 3A-3F illustrate a fabrication sequence for forming the edge connect via of FIG. 2A, according to some non-limiting embodiments of the present application.
Figure 3B:
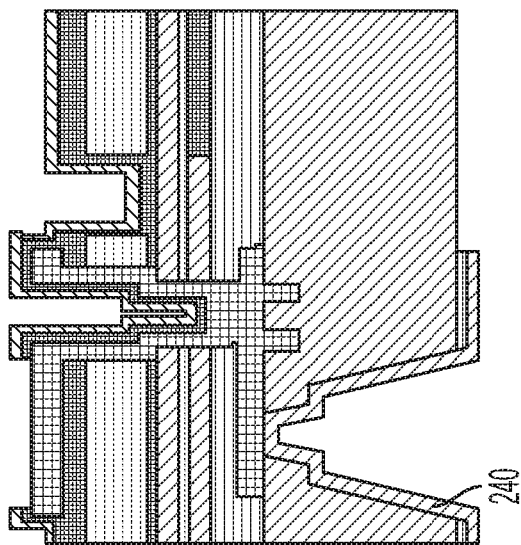

At the process step FIG. 3B, the inner walls of trench 220 and opening 221 are lined with a layer of insulative material 240. The insulative material may include epoxy and/or silicon oxide in some embodiments. For example, a silicon oxide may be first deposited, and then a layer of epoxy may be deposited on the silicon oxide layer. The layer of insulative material may be included to increase electrical isolation between the resulting edge-contact via and handle 203. As a result, The edge-contact via may be able to withstand high voltages, thus enabling high voltage operation. For example, the edge-contact via may be able to withstand voltages in excess of 25V, 50V, or 100V, among other possible values.

Figure 3C:
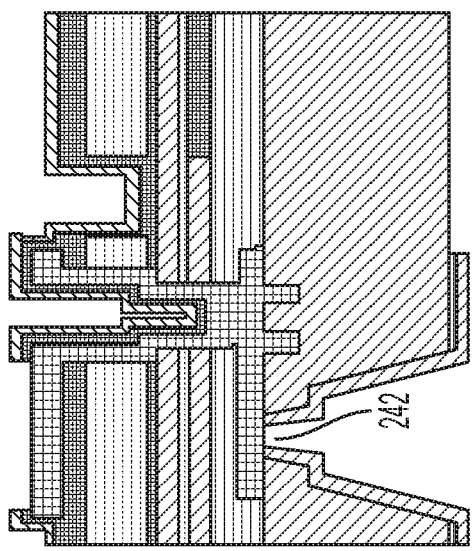

At the process step of FIG. 3C, an opening 242 is formed through insulative material layer 240, thus uncovering the bottom surface of pad 224 (or the bottom surface of bottom electrode 230).

Figure 3D:
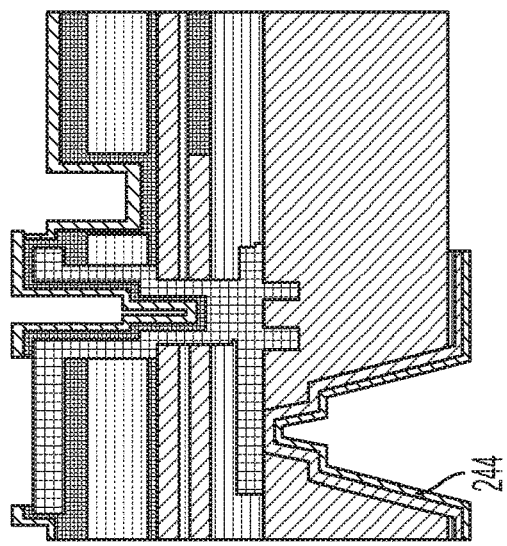
Figure 3E:
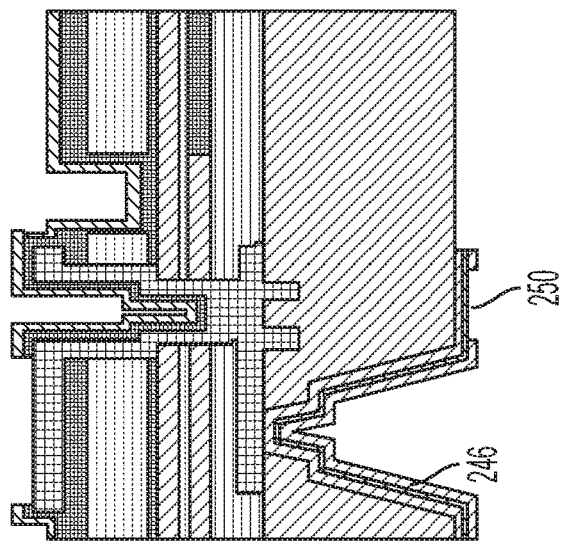

At the process step of FIG. 3D, a layer of conductive material 244 is deposited on the insulative material layer 240. Conductive material 244 may be deposited on the inner walls of trench 220 and partially on the bottom surface of handle 203. Conductive material 244 may be in electrical contact with the bottom surface of pad 224 (or the bottom surface of bottom electrode 230). Conductive material 244 may be formed of aluminum, copper, or any other suitable metallization material. Optionally, a passivation layer 246 may be deposited on conductive material 244 (see FIG. 3E). A portion of the passivation layer 246 may be removed in correspondence with the conductive material on the bottom surface of handle 203, thus opening a bond pad 250.

Figure 3F:
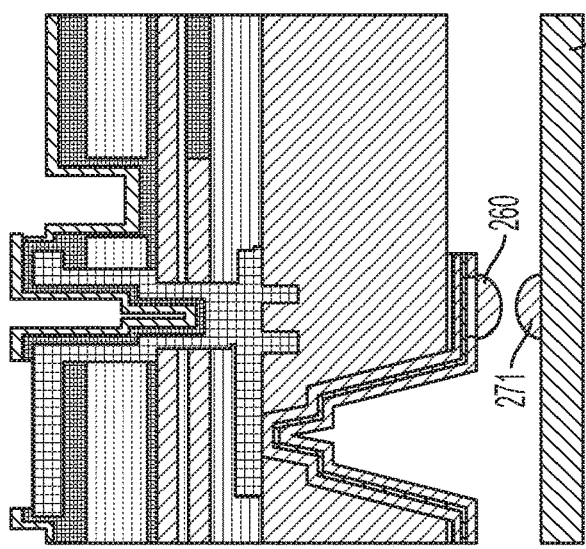

At the process step of FIG. 3F, ultrasound chip 200 is surface mounted to a substrate 270. Surface mounting may include flip-chip bonding in some embodiments. For example, ultrasound chip 200 may be mounted such that a solder bump 260 (or solder ball) is connected between a bond pad 250 and a corresponding solder bump 271 (or solder ball) formed on the top surface of substrate 270. Ball grid arrays may be used in some embodiments to provide connection.

Figure 4:
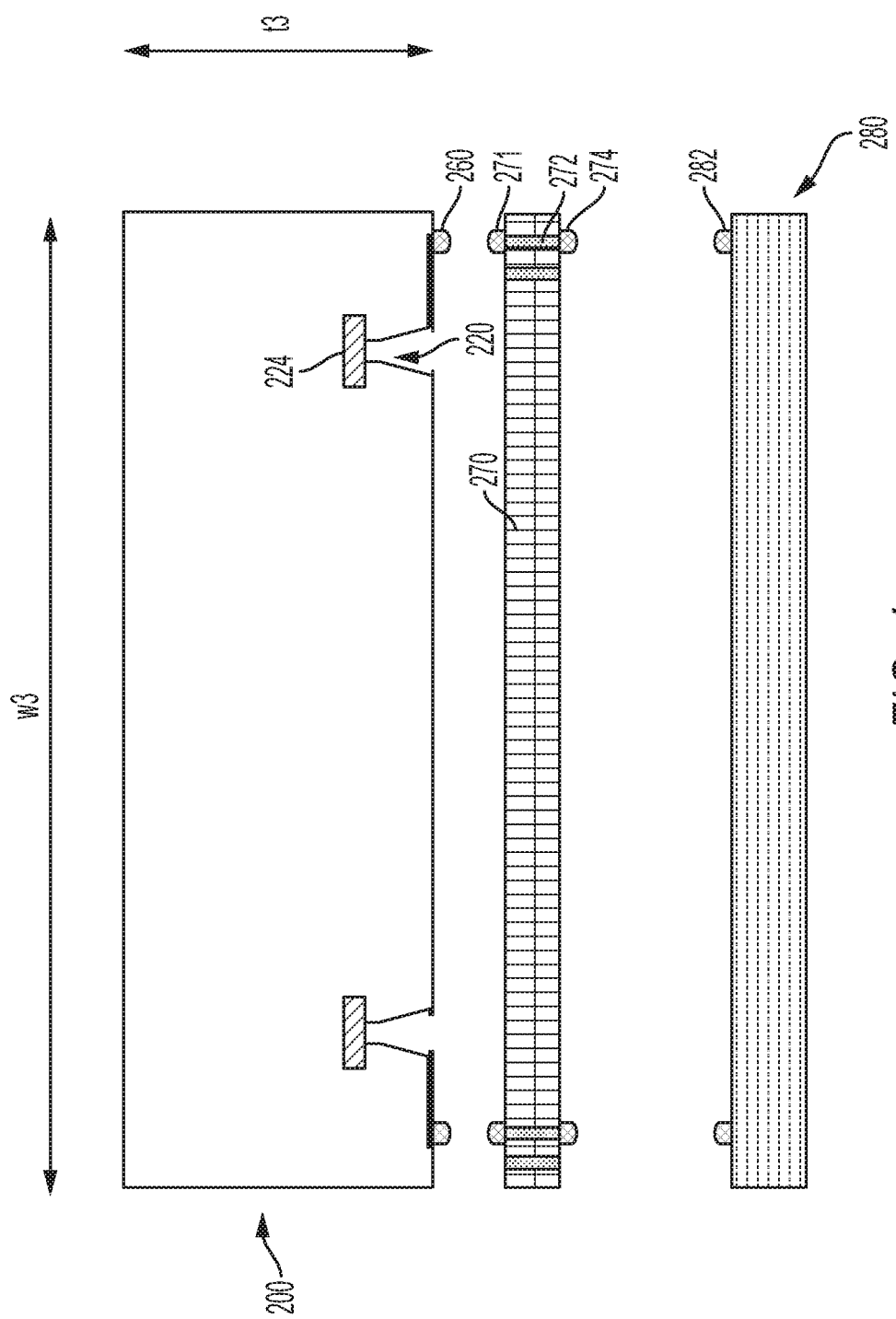
FIG. 4 is a cross sectional view of an ultrasound chip including edge-contact vias during packaging, according to some non-limiting embodiments of the present application.

Substrate 270 may include any suitable type of substrate, including an interposer (e.g., a silicon interposer) or a printed circuit board. In some embodiments, ultrasound chip 200 is mounted on an interposer, and the resulting assembly is mounted on a printed circuit board. One such arrangement is illustrated in FIG. 4, in accordance with some non-limiting embodiments. As shown in this figure, ultrasound chip 200 may be surface mounted to substrate 270 (an interposer in this case), with solder bump 260 being connected to solder bump 271. The surface mounted assembly may be mounted to printed circuit board 280, with solder bump 274 being connected to solder bump 282. Substrate 270 may include in-plane conductive traces (not shown in FIG. 4) for routing electric signals as desired. Additionally, substrate 270 includes vias, such as via 272, for allowing transfer of electric signals between printed circuit board 280 and ultrasound chip 200. In some embodiments, printed circuit board 280 includes other electronic devices (not shown in FIG. 4), such as one or more digital chips for processing the information obtained using the ultrasound transducers, and optionally for compressing the information.

Ultrasound chip 200 may have a width (w3) between 100 µm and 1 cm, between 100 µm and 7.5 mm, between 100 µm and 5 mm, between 100 µm and 2.5 mm or between 100 µm and 1 mm, or any other suitable range within such ranges. Other ranges are also possible. Ultrasound chip 200 may have a thickness (t3) between 100 µm and 1 cm, between 100 µm and 7.5 mm, between 100 µm and 5 mm, between 100 µm and 2.5 mm, between 100 µm and 1 mm, between 100 µm and 750 µm, between 100 µm and 500 µm, between 100 µm and 300 µm, or any other suitable range within such ranges.

II. THROUGH SILICON VIAS

Some embodiments relate to vertical integrated interconnects including through silicon vias (TSV). Similar to edge-contact vias, through silicon vias provide access to the ultrasound transducers through the bottom surface of the ultrasound-on-a-chip.

Figure 5:
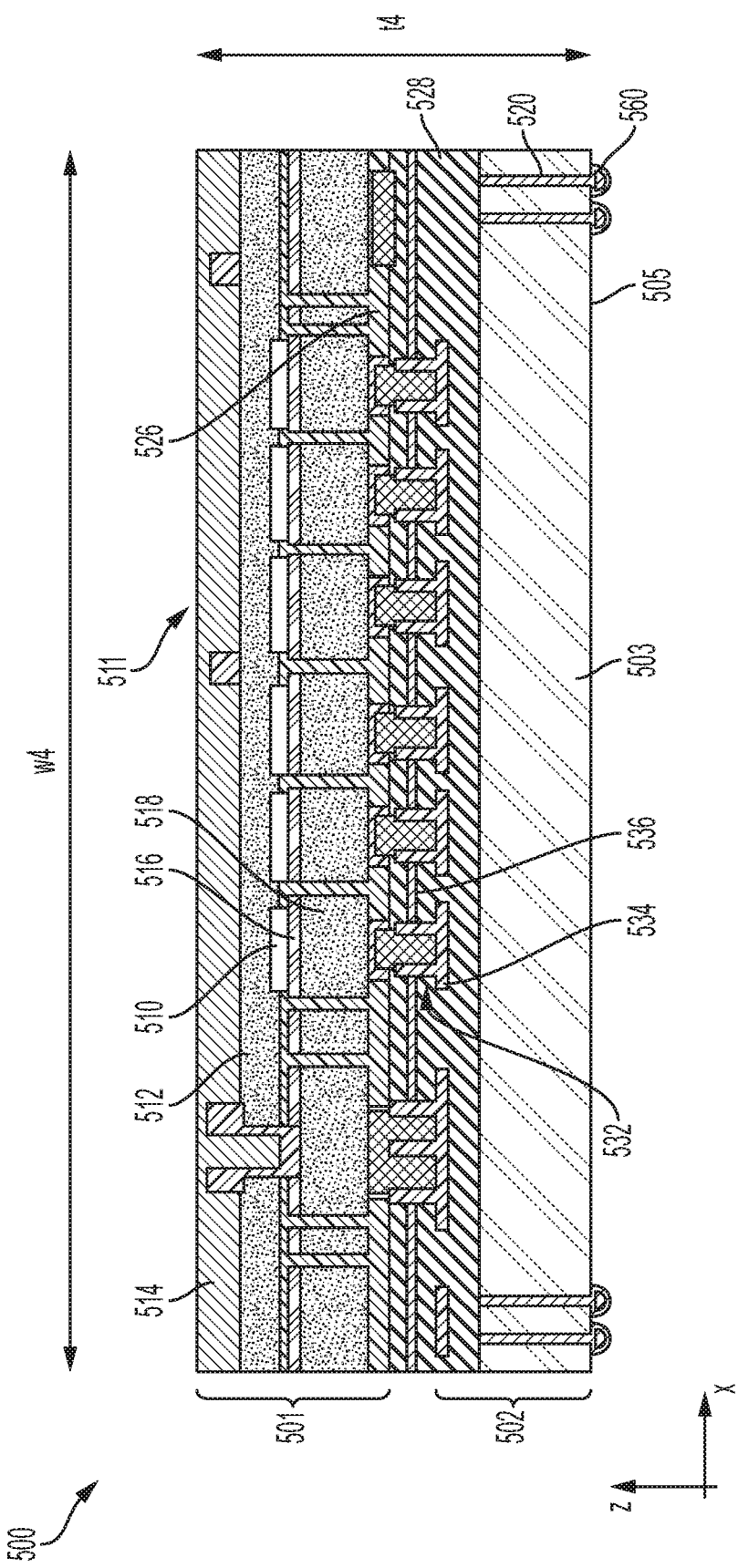
FIG. 5 is a cross sectional view of an ultrasound chip including through silicon vias, according to some non-limiting embodiments of the present application.

An example of an ultrasound chip including through silicon vias is illustrated in FIG. 5, in accordance with some non-limiting embodiments. Ultrasound chip 500 includes an ultrasound transducer substrate 501 bonded to a circuit substrate 502, such as a CMOS substrate. The ultrasound transducer substrate 501 includes a plurality of cavities 510, a first silicon device layer 518, a second silicon device layer 512, a silicon oxide layer 526, a passivation layer 514 and silicon oxide portions 516. The cavities 510 are formed between the first silicon device layer 518 and the second silicon device layer 512. The silicon oxide layer 526 (e.g., a thermal silicon oxide such as a silicon oxide formed by thermal oxidation of silicon) is formed between the first and second silicon device layers 518 and 512, with the cavities 510 being formed therein. The silicon oxide portions 516 may represent the silicon oxide layer on one substrate that was bonded to the silicon oxide layer 526 that was on the other substrate prior to bonding. In this non-limiting example, the first silicon device layer 518 may serve as a bottom electrode and the second silicon device layer 512 may be configured as a membrane. Thus, the combination of the first silicon device layer 518, the second silicon device layer 512, and the cavities 510 may form ultrasound transducers (e.g., CMUTs), of which six are illustrated in this non-limiting cross-sectional view. To facilitate operation as a bottom electrode or membrane, one or both of the first silicon device layer 518 and second silicon device layer 512 may be doped to act as conductors, and in some cases may be highly doped (e.g., having a doping concentration greater than $10^{15}$ dopants/cm$^3$ or greater). The passivation layer 514 passivates the first silicon device layer 518. The top surface 511 of the ultrasound-on-a-chip represents the face from which ultrasound energy will be transmitted by the ultrasound transducers for imaging. Therefore, the top face 511 represents the sensor face of the ultrasound device of which the ultrasound chip 500 is a part.

The circuit substrate 502 includes metallization 534, an insulative layer 528, a bulk silicon layer 503, through-silicon vias (TSVs) 520, and solder bumps 560. The metallization 534 may be formed of aluminum, copper, or any other suitable metallization material, and may represent at least part of an integrated circuit formed in the circuit substrate 502. For example, the metallization 534 may serve as a routing layer, may be patterned to form one or more electrodes, or may be used for other functions. In practice, the circuit substrate 502 may include more than one metallization layer, but for simplicity only one metallization 534 is illustrated.

TSVs 520 are vias that pass through the handle 503 of circuit substrate 502 and extend in the vertical direction. The TSVs 520 may transmit electrical signals between one or more integrated circuits included in the circuit substrate 502 and the solder bumps 560, which are on interface surface 505 (the bottom surface) of ultrasound chip 500. The TSVs 520 may be formed for example, from copper, doped silicon, doped polysilicon, or tungsten. (Electrical connection between the TSVs 520 and integrated circuits in the integrated circuit substrate 502 are not shown in FIG. 5). The ultrasound chip 500 further includes bonding structures 532 and a passivation layer 536 formed in preparation for forming the bonding structures 532. The bonding structures 532 electrically connect the ultrasound transducer substrate 501 to the circuit substrate 502. Accordingly, electrical signals may be transmitted from the integrated circuit substrate 502, through the bonding structures 532, and to the ultrasound transducer substrate 501, and vice versa.

Ultrasound chip 500 may have a width (w4) between 100 µm and 1 cm, between 100 µm and 7.5 mm, between 100 µm and 5 mm, between 100 µm and 2.5 mm or between 100 µm and 1 mm, or any other suitable range within such ranges. Other ranges are also possible. Ultrasound chip 200 may have a thickness (t4) between 100 µm and 1 mm, between 100 µm and 750 µm, between 100 µm and 500 µm, between 100 µm and 300 µm, between 100 µm and 200 µm, or any other suitable range within such ranges.

Ultrasound chip 500 may be surface mounted to any suitable substrate, such as an interposer or a printed circuit board. In some embodiments, ultrasound chip 500 is mounted on an interposer (e.g., a silicon interposer), and the resulting assembly is mounted on a printed circuit board. One such arrangement is illustrated in FIG. 6, in accordance with some non-limiting embodiments. In this example, ultrasound chip 500 may be surface mounted to substrate 270 (an interposer in this case), with solder bump 560 being connected to solder bump 271. The surface mounted assembly may be mounted to printed circuit board 280, with solder bump 274 being connected to solder bump 282.

FIGS. 7A-7F illustrate a fabrication sequence for fabricating an ultrasound chip with TSVs, in accordance with some non-limiting embodiments. Ultrasound chip 500 may be fabricated using the sequence of FIGS. 7A-7F or using any other suitable fabrication sequence.

At the process step of FIG. 7A, a circuit substrate 502 having circuits formed therein is provided, and a region of circuit substrate 502 is doped via ion implantation. Subsequently, as shown in FIG. 7B, the doped region (or at least a portion of the doped region) may be etched to form a column (544) of doped silicon. When formed, doped silicon column 554 is surrounded by a recess, which in some embodiments is shaped as a ring. Doped silicon column 554 may serve as TSV 520 of FIG. 5. Subsequently, as shown in FIG. 7C, the recess may be filled with an insulative material 556, such as silicon oxide.

Figure 7D:
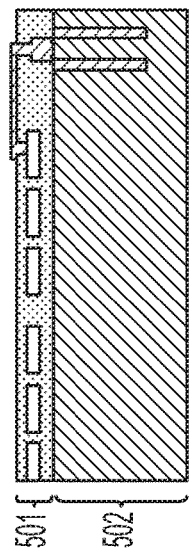
Figure 7E:
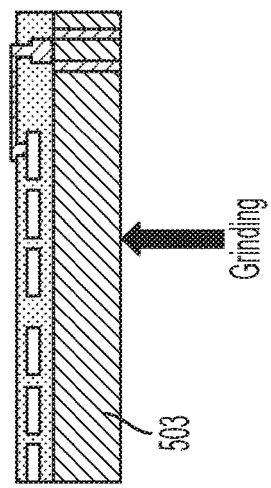

At the process step of FIG. 7D, circuit substrate 502 is bonded to ultrasound transducer substrate 501. Doped silicon columns 554 may provide access to first silicon device layer 518 and second silicon device layer 512. At the process step of FIG. 7E, grinding may be performed on the handle 503 of circuit substrate 502. The result is a substantial reduction in the thickness of the chip. In some embodiments, more than half of the original handle thickness may be removed by grinding. The resulting chip may have a thickness between 100 µm and 300 µm in some embodiments. After grinding, the bottom side of doped silicon columns 554 may be exposed, thus enabling access to the doped silicon columns 554 from the bottom surface of the chip.

Figure 7F:
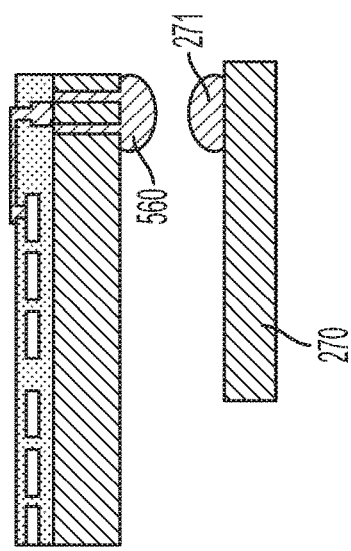

At the process step of FIG. 7F, the chip is surface mounted to a substrate 270. Surface mounting may include flip-chip bonding in some embodiments. For example, the chip may be mounted such that a solder bump 560 (or solder ball) connects a doped silicon column 544 with a corresponding solder bump 271 (or solder ball) formed on the top surface of substrate 270. Ball grid arrays may be used in some embodiments to provide connection.

III. CONDUCTIVE PILLARS

Some embodiments relate to vertical integrated interconnects including conductive pillars. Conductive pillars of the types described herein provide access to ultrasound transducers through the top surface of an ultrasound chip (the surface opposite the mounting surface).

Figure 8:
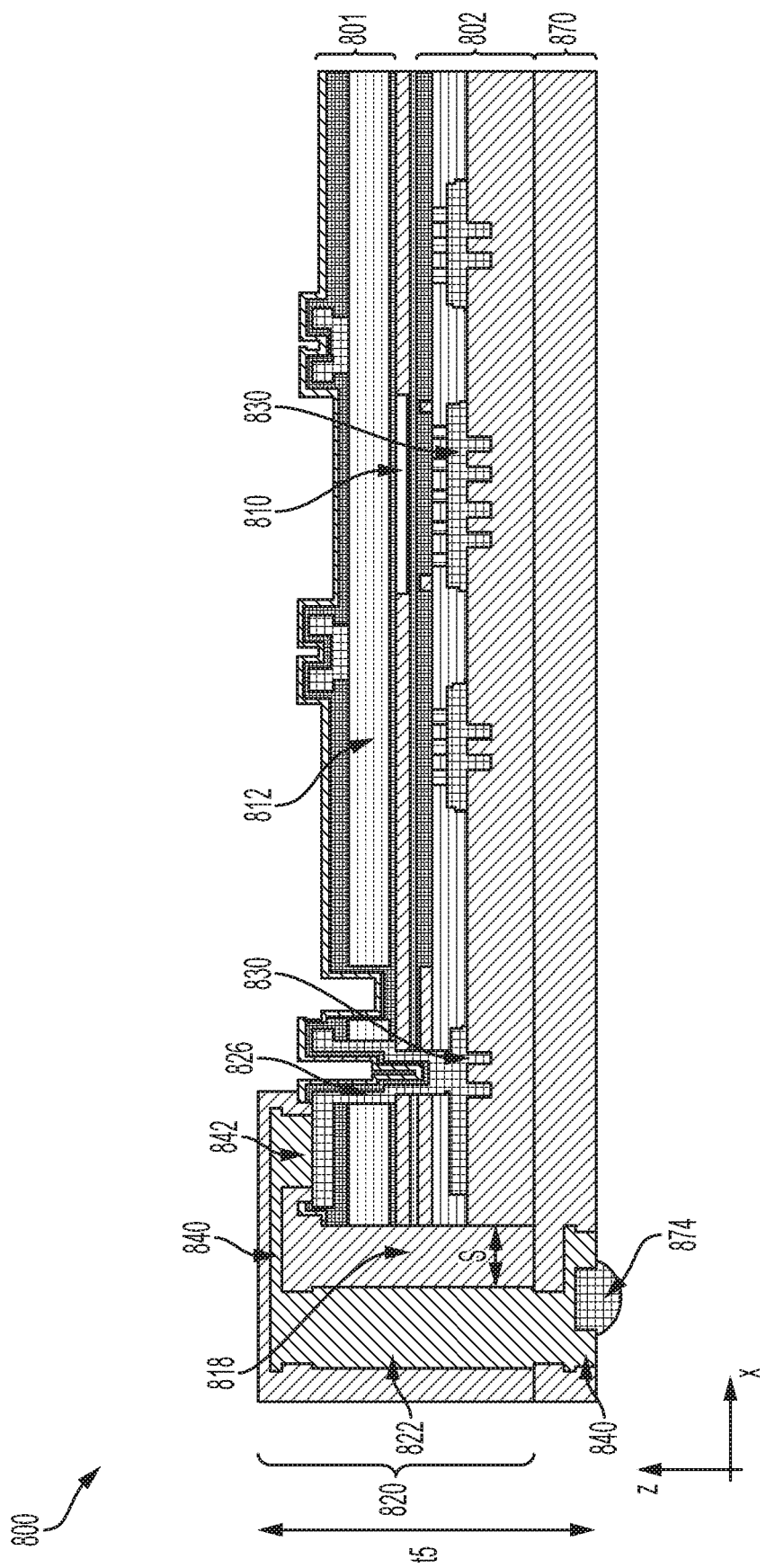
FIG. 8 is a cross sectional view of an ultrasound chip including conductive pillars, according to some non-limiting embodiments of the present application.
Figure 3D:
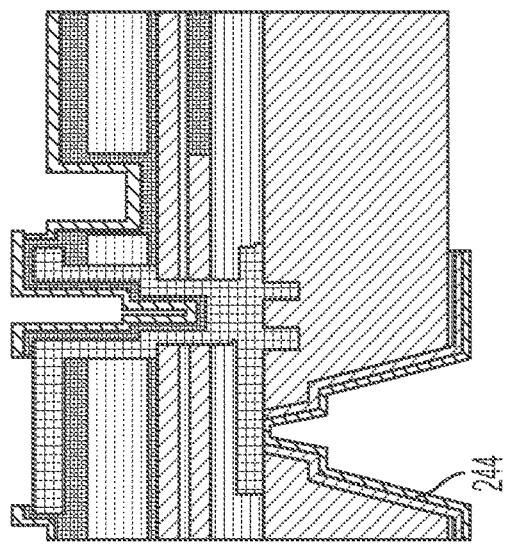
Figure 3E:
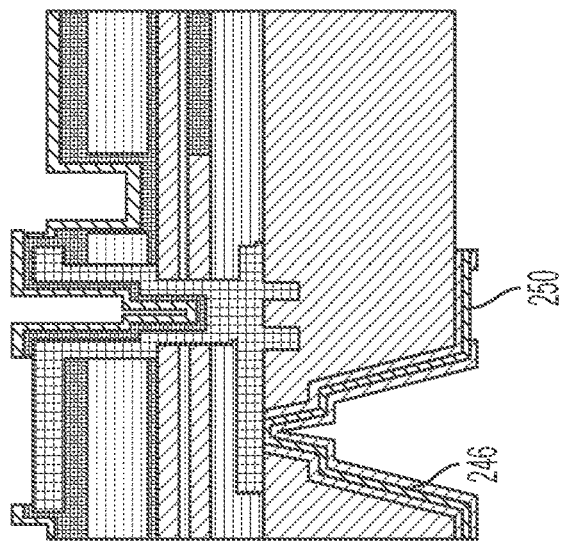
Figure 3F:
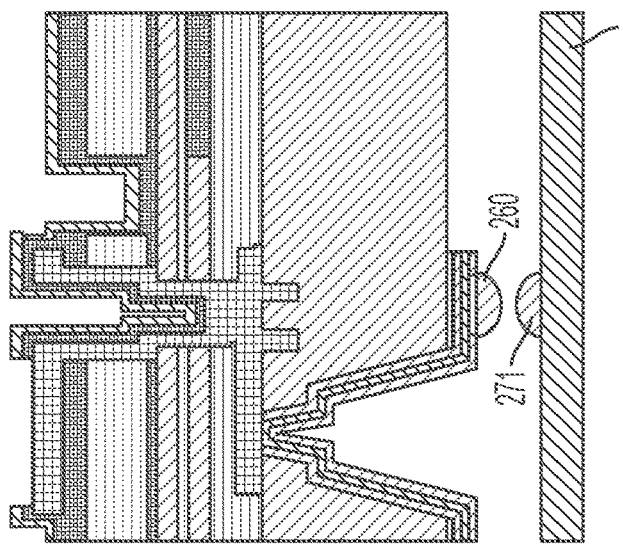

An example of an ultrasound chip including conductive pillars is illustrated in FIG. 8, in accordance with some embodiments. Ultrasound chip 800 includes an ultrasound transducer substrate 801, a circuit substrate 802, a handle substrate 870 and a conductive pillar 822 (embedded within support 820). Ultrasound transducer substrate 801 and circuit substrate 802 may have characteristics similar to those of ultrasound transducer substrate 201 and circuit substrate 202, as described in connection with FIG. 2A. For example, cavity 810, membrane 812, bottom electrode 830 and conductive structure 826 may have characteristics similar to those of cavity 210, membrane 212, bottom electrode 230 and conductive structure 226, respectively. Circuit substrate 802 is mounted on handle substrate 870, which may be made of any suitable dielectric material, including for example polyimide. Solder bumps 874 (or other types of interconnects) may connect the bottom surface of handle substrate 870 to an underlying interposer or printed circuit board.

Electric access to the ultrasound transducers is provided via conductive pillars 822. FIG. 8 illustrates a chip with a single conductive pillar. However, multiple conductive pillars may be used to enable independent control of different ultrasound transducers. The conductive pillars may be disposed near the outer perimeter of ultrasound transducer substrate 801. To provide mechanical support, conductive pillar 822 is embedded within support 820 in some embodiments. Support 820 may bonded to handle substrate 870 in any suitable manner, and includes a portion extending primarily in the vertical direction. Handle substrate 870 includes a metal layer 840 for providing electrically connection between solder bump 874 and conductive pillar 822 when support 820 is mounted to handle substrate 870.

Conductive pillar 822 may include copper in some embodiments. In some such embodiments, the conductive pillar is a copper pillar. However, other materials may be used for the conductive pillar, including for example aluminum and tungsten. Conductive pillar 822 extends primarily in the vertical direction.

Support 820 may include an insulative material 818, such as epoxy, polyimide and/or silicon oxide. Insulative material 818 separates conductive pillar 822 from substrates 801 and 802 in-plane. The separation (s) may be sufficiently large to enable high voltage operations. Such separations, in fact, may increase the electric isolation between conductive pillar 822 and substrates 801 and 802. For example, separation s may be between 100 µm and 1 mm, between 100 µm and 750 µm, between 100 µm and 500 µm, or between 100 µm and 250 µm, among other possible values. As a result, conductive pillar 822 may be able to withstand voltages in excess of 50V, 75V, 100V or 125V without experiencing electric breakdown.

Support 820 may further support conductive layer 840, which may include copper, or aluminum, among other possible conductors. Conductive layer 840 may be patterned to form conductive traces that extend in a plane parallel to the xy-plane. The plane of conductive layer 840 lies above the top surface of ultrasound transducer 801 in some embodiments. To provide contact with membrane 812 or bottom electrode 830, a vertical connection 842 may be provided. Vertical connection 842 may be supported by support 820 and may extend from the plane of the conductive trace 840 in the downward direction parallel to z-axis. In the example of FIG. 8, vertical connection 842 connects to conductive structure 826, which in turn connects to a bottom electrode 830. Similar arrangements, not illustrated in FIG. 8, may be used to contact a membrane 812.

In some embodiments, ultrasound chip 800 includes more than one conductive layer 840. The different conductive layers may be at different planes along the z-axis. In these embodiments, having multiple planes of conductive layers may simplify the routing between the conductive pillars and the respective ultrasound transducers.

V. CONCLUSION

Aspects of the technology described herein may provide one or more benefits, some of which have been previously described. Now described are some examples of such benefits. It should be appreciated that not all aspects and embodiments necessarily provide all of the benefits now described. Further, it should be appreciated that aspects of the technology described herein may provide additional benefits to those now described.

Some aspects of the technology described herein provide vertical packaging techniques for ultrasounds-on-a-chip that do not resort to wire bonding. As a result, ultrasound-on-a-chip that employ such packaging techniques are substantially narrower and/or substantially thinner than other types of ultrasound-on-a-chip. The width reduction may enable probing of small features.

Some aspects of the technology described herein provide ultrasounds-on-a-chip that are substantially less power hungry than ultrasound chips using bond wires. This is because the integrated interconnects used in such ultrasounds-on-a-chip are shorter than bond wires, and as a result, have less inductance. The power reduction may enable use of these ultrasounds-on-a-chip is low-power applications.

Some aspects of the technology described herein provide ultrasounds-on-a-chip that can withstand high voltages, such as in excess of 100V in some embodiments. The ability to withstand such high voltages may be achieved thanks to the presence of insulative layers between the circuit substrate and the integrated interconnects.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having,"

"containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A device comprising:
   an ultrasound-on-a-chip comprising one or more ultrasound transducers, wherein the ultrasound-on-a-chip has a first surface that is mounted to a substrate and a second surface opposite the first surface; and
   a first integrated interconnect that electrically connects the substrate to the one or more ultrasound transducers, wherein
   the first integrated interconnect comprises a conductive pillar that extends, continuously, from the first surface to the second surface such that the first surface is electrically connected to the one or more ultrasound transducers through the second surface, and
   the first integrated interconnect is spaced from the ultrasound-on-a-chip in a direction substantially parallel to the first surface.

2. The device of claim 1, further comprising a metal portion electrically connecting the first integrated interconnect to the substrate.

3. The device of claim 1, wherein the first integrated interconnect further comprises a conductive layer coupled to the conductive pillar and extending in the direction substantially parallel to the first surface.

4. The device of claim 1, wherein the ultrasound-on-a-chip further comprises a conductive portion electrically connecting the first integrated interconnect with a bottom electrode of the one or more ultrasound transducers.

5. The device of claim 1, wherein the conductive pillar is embedded within an insulative support that is coupled to the ultrasound-on-a-chip.

6. The device of claim 1, wherein the one or more ultrasound transducers each comprise:
   A bottom electrode electrically connected to the first integrated interconnect;
   a membrane; and
   one or more cavities formed between the bottom electrode and the membrane.

7. The device of claim 6, wherein
   the ultrasound-on-a-chip comprises a plurality of the ultrasound transducers, and
   in each of the ultrasound transducers, a plurality of the cavities is formed between the bottom electrode and the membrane.

8. The device of claim 6, wherein
   the membrane is electrically connected to a second integrated interconnect, and
   the first integrated interconnect is electrically isolated from the second integrated interconnect.

9. The device of claim 1, wherein the conductive pillar has a height less than 1.5 mm.

10. The device of claim 1, wherein the conductive pillar has a height less than 1 mm.

11. The device of claim 1, wherein the conductive pillar has a height greater than a height of the ultrasound-on-a-chip.

12. The device of claim 1, wherein
    a second integrated interconnect electrically connects the substrate to the one or more ultrasound transducers, and
    the first integrated interconnect is electrically isolated from the second integrated interconnect.

13. The device of claim 1, wherein the second integrated interconnect comprises a conductive pillar that extends, continuously, from the first surface to the second surface such that the first surface is electrically connected to the one or more ultrasound transducers through the second surface.

14. The device of claim 1, wherein the spacing between the first integrated interconnect and the ultrasound-on-a-chip is greater than or equal to 100 micrometers.

15. An ultrasound device, comprising:
    an ultrasound-on-a-chip comprising one or more ultrasound transducers, wherein the ultrasound-on-a-chip has a first surface that is mounted to a substrate and a second surface opposite the first surface;
    an interposer spaced from the ultrasound-on-a-chip in a first direction; and
    a first integrated interconnect that electrically connects the interposer to the one or more ultrasound transducers, the first integrated interconnect comprising a conductive pillar spaced from the ultrasound-on-a-chip in a second direction perpendicular to the first direction, wherein
    the conductive pillar extends, continuously, from the first surface to the second surface such that the first surface is electrically connected to the one or more ultrasound transducers through the second surface.

16. The ultrasound device of claim 15, wherein a width of the ultrasound device along the second direction is less than 30 mm.

17. The ultrasound device of claim 15, wherein the conductive pillar has a height along the first direction greater than a height of the ultrasound-on-a-chip along the first direction.

18. The device of claim 15, wherein,
    a second integrated interconnect electrically connects the substrate to the one or more ultrasound transducers, and
    the first integrated interconnect is electrically isolated from the second integrated interconnect.

19. The device of claim 15, wherein the second integrated interconnect comprises a conductive pillar that extends, continuously, from the first surface to the second surface such that the first surface is electrically connected to the one or more ultrasound transducers through the second surface.

20. The device of claim 15, wherein the spacing between the first integrated interconnect and the ultrasound-on-a-chip is greater than or equal to 100 micrometers.

* * * * *